United States Patent [19]

Yanobu

[11] Patent Number: 5,676,859
[45] Date of Patent: Oct. 14, 1997

[54] INJECTION NEEDLE SAFETY DISPOSAL APPARATUS

[75] Inventor: Toshio Yanobu, Kyoto, Japan

[73] Assignees: Taiyo Elecs Co., Ltd., Kyoto; Oki Customer Advanced-Technology Co., Ltd., Tokyo, both of Japan

[21] Appl. No.: 565,427

[22] Filed: Nov. 30, 1995

[30] Foreign Application Priority Data

Jun. 27, 1995 [JP] Japan .................. 7-160333

[51] Int. Cl.$^6$ .................. B23K 11/22; A61G 12/00; A61L 11/00
[52] U.S. Cl. .................. 219/68
[58] Field of Search .................. 219/68

[56] References Cited

U.S. PATENT DOCUMENTS

| | | | |
|---|---|---|---|
| 4,877,934 | 10/1989 | Spinello | 219/68 |
| 4,961,541 | 10/1990 | Hashimoto | 219/68 |
| 5,091,621 | 2/1992 | Butler | 219/68 |
| 5,138,124 | 8/1992 | Kirk et al. | 219/68 |
| 5,212,362 | 5/1993 | Burden et al. | 219/68 |
| 5,288,964 | 2/1994 | Walker et al. | 219/68 |
| 5,336,862 | 8/1994 | Yelvington | 219/68 |
| 5,365,029 | 11/1994 | Makihara | 219/68 |
| 5,545,869 | 8/1996 | Piva | 219/68 |
| 5,548,095 | 8/1996 | Cornell | 219/68 |

FOREIGN PATENT DOCUMENTS 43-13440  7/1968  Japan .................. 219/68

Primary Examiner—Geoffrey S. Evans
Attorney, Agent, or Firm—Jordan and Hamburg

[57] ABSTRACT

Roller electrodes 5 and 6 are rotated by DC motor 2. Power is supplied to the electrodes 5 and 6 through brushes 10a and 10b. If the tip of an injection needle N is brought into contact with first roller electrode 5, and a part slightly away from the tip of injection needle N toward the root is brought in contact with roller electrode 6, the part of the injection needle N sandwiched between electrodes 5 and 6 fuses because of the Joule heat generated. If the syringe is pushed so that the injection needle N is always in contact with electrodes 5 and 6, almost the complete injection needle N can be fused. The first roller electrode 5 has a tapered form; the width of the gap between electrodes 5 and 6 can be varied; therefore, a position where the gap suits the diameter of the needle can be selected. Consequently, maintenance work becomes easy. Also, stable disposal of the needles is possible irrespective of the diameter of the injection needle.

32 Claims, 9 Drawing Sheets

INJECTION NEEDLE SAFETY DISPOSAL APPARATUS

BACKGROUND OF THE INVENTION

1. Field of the Invention

The present invention relates to an injection needle safety disposal apparatus. More particularly, it relates to an injection needle safety disposal apparatus wherein the life of the electrode in contact with the injection needle is prolonged and needles are disposed stably, irrespective of the diameter of the needle.

2. Description of Prior Art

FIG. 14 is an explanatory diagram of an injection needle safety disposal apparatus proposed in the Japanese Patent Laid-open no. 320057/1989.

If the cover 507 of the injection needle safety disposal apparatus 500 is opened and a used needle N inserted in the insertion slot 502, the injection needle N is retained in the retaining unit 510a of the ring 510. The tip of the injection needle N touches the electrode 503 supported by a spring 522.

If the cover 507 is closed, the electrode 504 clamps the injection needle N because of an interlock, the switch 511 becomes ON, and electric current flows to the electrodes 503 and 504 through the battery 512. By this flowing electric current, the injection needle N is heated to a red-hot condition and sterilized. And furthermore, the tip of the injection needle N fuses and becomes rounded. The gas generated when the injection needle is heated to a red-hot condition is led to the deodorizing agent 518 by means of the fan 520, deodorized and discharged. Two to three seconds after electric current flows, the switch 511 switches off automatically.

Next, the ring 510 rotates by 180 degrees, and the treated injection needle N is dropped into the container 516 and destroyed.

Japanese Patent Laid-open no. 126146/1992 proposes an injection needle disposal apparatus wherein the injection needle is fused by using plasma discharge.

Japanese Patent Laid-open no. 92026/1993 proposes an injection needle disposal apparatus wherein the injection needle, softened by passing electric current, is cut by blades.

In said injection needle safety disposal apparatus 500 according to prior art, the fused part of the injection needle is deposited on the contact part 4 of the electrode 504, which is in contact with the injection needle N, causing a performance degradation in the electrode 504; therefore, it arises the problem wherein frequent replacement of the electrode 504 is required.

Similarly in other injection needle safety disposal apparatus according to prior art also, the contact part of the electrode touching the injection needle deteriorates, therefore, it arises the problem wherein frequent replacement of the electrode is required.

Another problem is the inability to dispose the needles stably depending on the diameter of the injection needle.

SUMMARY OF THE INVENTION

The first object of the present invention is to provide an improved injection needle safety disposal apparatus wherein frequent replacement of the electrode is not necessary.

The second object of the present invention is to provide an improved injection needle safety disposal apparatus that allows injection needles to be disposed stably irrespective of the diameter of the injection needle.

More specifically, the first aspect of the present invention is to provide an injection needle safety disposal apparatus comprising;

- a first electrode with a contact part that touches the tip of the injection needle, and means to change said contact part; a second electrode with a contact part that touches a part on said injection needle slightly away from the tip and toward the root of the needle, and means to change said contact part; electrode moving means for moving said first electrode and said second electrode to change the contact part of said first electrode and said second electrode;
- power supply means for supplying power to said first electrode and said second electrode capable of fusing a part of said injection needle when it touches the contact part of said first electrode and contact part of said second electrode.

In the injection needle safety disposal apparatus according to the aforementioned first aspect, the tip of the injection needle provided in the syringe is brought into contact with the first electrode; the part slightly away from the tip and toward the root is brought into contact with the second electrode and power is supplied by the power supply means. The part of the injection needle sandwiched between the two electrodes fuses because of Joule heat. By pushing in the syringe so that the tip of the injection needle is always in contact with the first electrode, almost the complete injection needle can be fused.

By providing means for moving the electrode, the contact part of the electrode touching the injection needle can be moved all the time; therefore, the fused part of the injection needle cannot stick to the electrode easily, and degradation in performance of the electrode is prevented. Consequently, the life of the electrode is prolonged and maintenance work becomes easy.

The second aspect of the present invention is to provide an injection needle safety disposal apparatus of the aforementioned configuration wherein;

- at least one electrode from said first electrode and said second electrode is a roller-type electrode;
- said electrode moving means is a roller rotating means for rotating said roller-type electrode.

In the injection needle safety disposal apparatus according to the aforementioned second aspect, at least one electrode from the first electrode and the second electrode is made a roller-type electrode, and means is provided to rotate the roller-type electrodes.

Roller-type electrodes are easy to manufacture and have excellent mechanical strength.

The third aspect of the present invention is to provide an injection needle safety disposal apparatus of the aforementioned configuration wherein;

- at least one electrode from said first electrode and said second electrode is a loop-type electrode;
- said electrode moving means is a loop rotating means for rotating said loop-type electrode.

In the injection needle safety disposal apparatus according to the aforementioned third aspect, at least one electrode from the first electrode and the second electrode is made a loop-type electrode, and means is provided to rotate the loop-type electrodes.

The length of the perimeter of a loop-type electrode can easily be increased while maintaining a small occupied space.

The fourth aspect of the present invention is to provide an injection needle safety disposal apparatus of the aforementioned configuration comprising;

means for scraping off material deposited on the electrode, which is provided at least near one of the electrodes from said first electrode and said second electrode.

In the injection needle safety disposal apparatus according to the aforementioned fourth aspect, means for scraping off material deposited on the electrode is provided at least near one of the electrodes from the first electrode and the second electrode.

By providing such means, even if a fused part of the injection needle sticks to the electrode, it is scraped off before it hardens; therefore, degradation in performance of the electrode is prevented. Consequently, the life of the electrode is prolonged and maintenance work becomes easy.

The fifth aspect of the present invention is to provide an injection needle safety disposal apparatus of the aforementioned configuration comprising;

means for changing the gap between said first electrode and said second electrode in a direction intersecting the direction of insertion of the injection needle.

In the injection needle safety disposal apparatus according to the aforementioned fifth aspect, means is provided to change the gap between the first electrode and the second electrode in a directional perpendicular to the direction of insertion of the injection needle.

By providing such means, a position that has a gap suitable for the diameter of the injection needle can be selected and used, therefore injection needles of various diameters can be dealed, and stable disposal of the needles is possible irrespective of the diameter of the injection needle.

The sixth aspect of the present invention is to provide an injection needle safety disposal apparatus of the aforementioned configuration comprising;

covering means such that when an injection needle is inserted in an injection needle insertion hole into which an insertion need can be inserted, the base of the syringe provided with an injection needle adheres closely isolating the outside of the injection needle safety disposal apparatus from the inside, and said covering means moves up or down following the motion of the syringe when said syringe is pushed in or pulled out.

In the injection needle safety disposal apparatus according to the aforementioned sixth aspect, covering means is provided which enables the base of the syringe to adhere closely, isolating the outside of the injection needle safety disposal apparatus from the inside, and said covering means moves up or down following the motion of said syringe when said syringe is pushed in or pulled out.

Although sparks are generated when the injection needle and electrodes come in contact, by providing the covering means, the sparks cannot leak outside the injection needle safety disposal apparatus, and safety is improved.

The seventh aspect of the present invention is to provide an injection needle safety disposal apparatus of the aforementioned configuration comprising;

tray means, which can receive and collect fused and hardened materials that drop after they are generated when a part of the injection needle fuses, and which can be removed easily from the injection needle safety disposal apparatus;

safety switch means for disabling said power supply means, which supplies power to said first electrode and second electrode for fusing a part of the injection needle, in the condition when the tray means has been removed from the injection needle safety disposal apparatus.

In the injection needle safety disposal apparatus according to the aforementioned seventh aspect, tray means, which can receive and collect metal scrap generated when a part of the injection needle fuses and which can be removed easily from the injection needle safety disposal apparatus, are provided; also, safety switch means, which disables supply of power when the tray means has been removed from the injection needle safety disposal apparatus, are provided.

If the tray means is removed for discarding the metal scrap, and subsequently, if re-fitting the tray means has been forgotten, the injection needle safety disposal apparatus will not operate; therefore, the safety switch means ensures that the re-fitting of the tray means is not forgotten.

The eighth aspect of the present invention is to provide an injection needle safety disposal apparatus of the aforementioned configuration comprising;

deodorizing means;

exhaust means for discharging the air in the vicinity of said electrodes after it has been led to said deodorizing means and deodorized, said exhaust means being a positive-displacement-type pump.

In the injection needle safety disposal apparatus according to the aforementioned eighth aspect, a positive-displacement-type pump is used as the exhaust means for discharging the air in the vicinity of the electrodes after it has been led to the deodorizing means and deodorized.

In the past, axial flow fans and centrifugal fans were used as exhaust means, but adequate static pressure cannot be obtained in turbo pumps such as axial flow fans and centrifugal fans, therefore, an adequate amount of deodorizing agents could not be passed through resulting in traces of odors of burnt blood. In contrast, in the present invention, a positive-displacement-type pump such as reciprocating pump or rotary pump is used as exhaust means; therefore, static pressures (for instance, equal to or greater than 100 $mmH_2O$) that is much higher than the exhaust resistance (for instance, about 30 $mmH_2O$) of the exsisting exhaust equipments generally used are obtained. Consequently, adequate quantity of deodorizing agents can be passed through resulting in satisfactory deodorization.

SPECIFIC DESCRIPTION OF THE EMBODIMENTS

The present invention will hereinafter be described in more detail by referring to the embodiments shown in the figures. However, it must be understood that these embodiments are intended to illustrate the invention and are not to be construed to limit the scope of the invention.

First Embodiment

Figure 1:
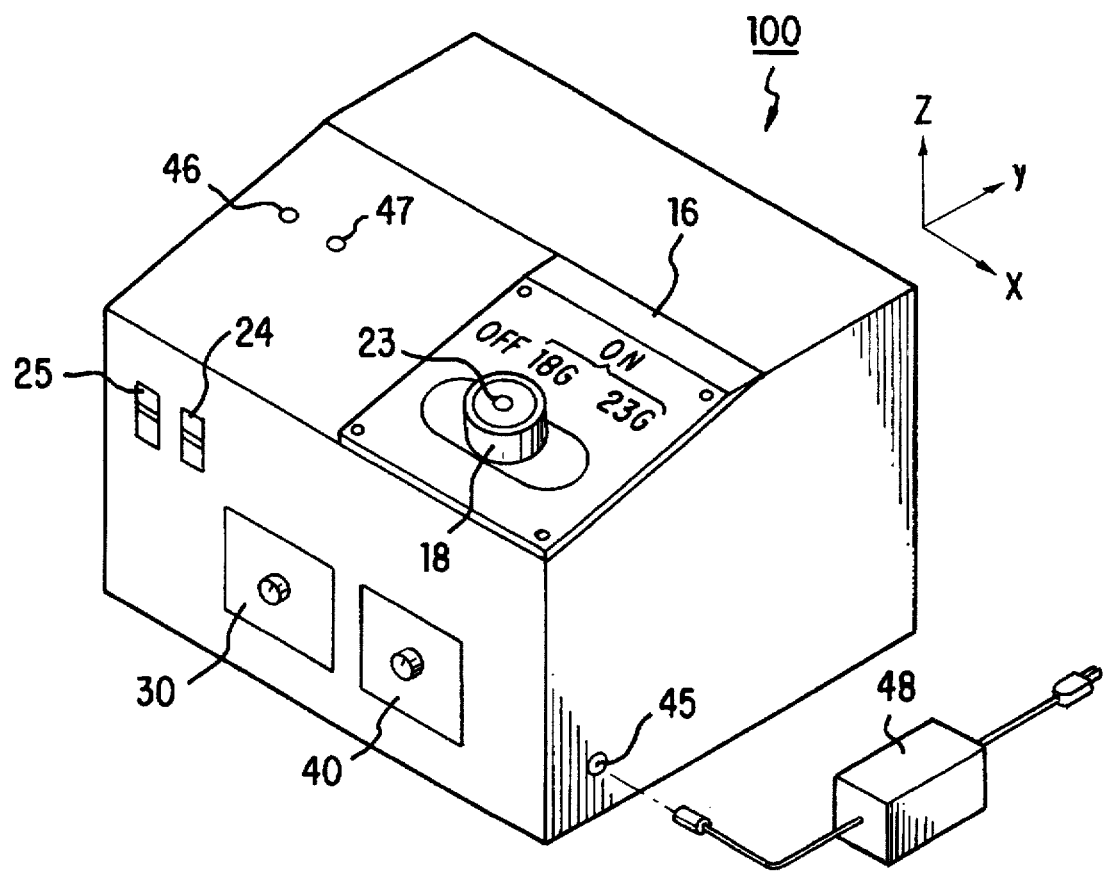
FIG. 1 is an external view showing the injection needle safety disposal apparatus according to the first embodiment of the present invention.

FIG. 1 is an external view of the injection needle safety disposal apparatus 100 in the first embodiment of the present invention. For the purpose of explanations, the transverse direction is taken as the x direction; the depth direction is taken as the y direction; and the vertical direction is taken as the z direction.

On the upper face of the injection needle safety disposal apparatus 100 is provided a panel 16, a power supply lamp 46, and a charging indicator lamp 47. A cylinder 18 protrudes from said panel 16. The cylinder 18 can move in the x direction; if it moves to the end of left, the power supply of the injection needle safety disposal apparatus 100 becomes OFF; if it moves toward the right side, the power supply of the injection needle safety disposal apparatus 100 becomes ON. A scale calibrated to relate the position of cylinder 18 and diameter of the injection needle is printed on said panel 16. The farther the position of cylinder 18 to the right, the smaller is the diameter of the injection needle. An injection needle insertion hole 23 for inserting the injection needle is provided in said cylinder 18.

On the front face of the injection needle safety disposal apparatus 100, has the exposed drawer face of a tray 40, which is used to receive and collect the metal scrap generated when the injection needle is fused. The front face of the injection needle safety disposal apparatus 100 also has the exposed drawer face of a deodorizing unit 30, which deodorizes the gas generated when the injection needle is fused; a reset switch 24 for the circuit protector (44 of FIG. 8) used as a circuit breaker when excess electric current flows; and a reverse rotation switch 25 for reversing the direction of rotation of roller-type electrodes (5, 6 in FIG. 3) described later.

A charging jack 45 for connecting a charger 48 is provided on the side face of the injection needle safety disposal apparatus 100.

Instead of said charging indicator lamp 47, a battery checker meter may be installed for analog detection of output voltages of battery (described later). This case has the advantage of accurately knowing the level of necessity for charging the battery.

Figure 2:
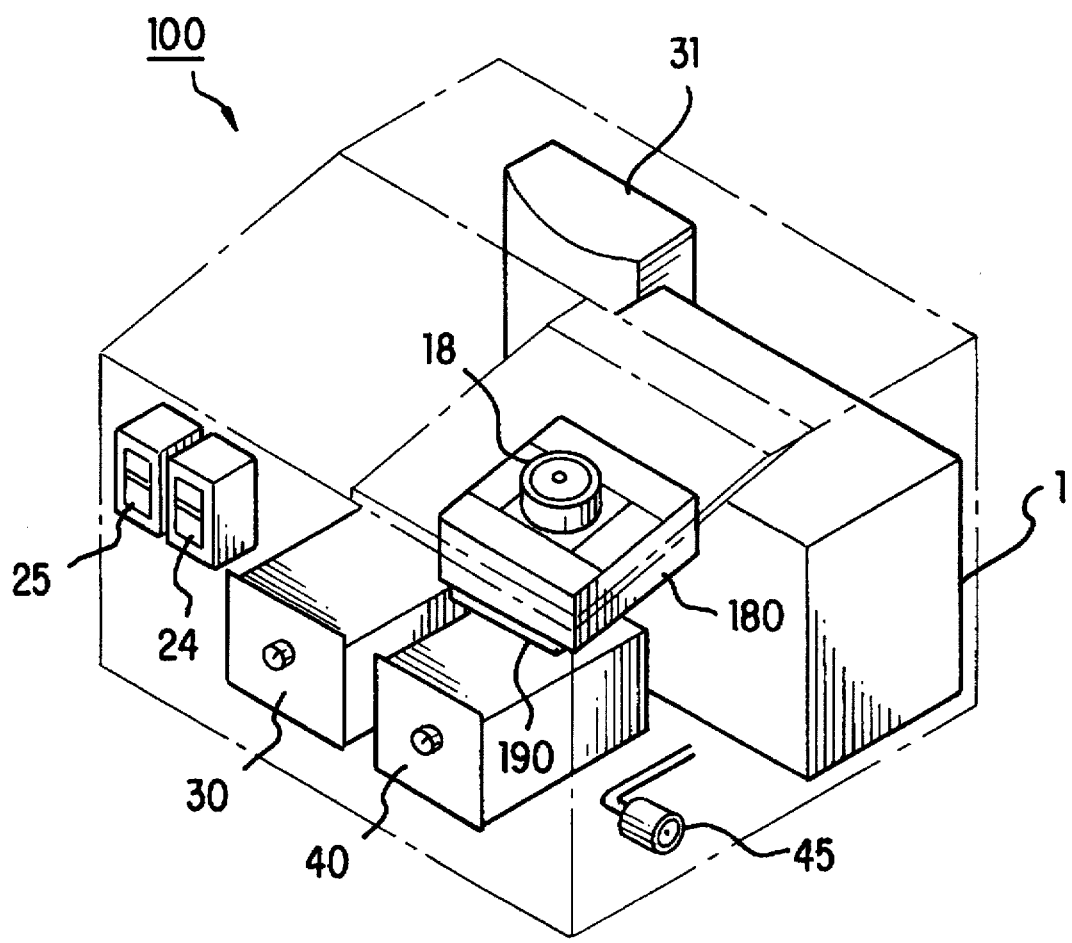
FIG. 2 is a perspective view showing the internal construction of the injection needle safety disposal apparatus of FIG. 1.

FIG. 2 is a perspective view showing the internal construction of the injection needle safety disposal apparatus 100.

A movable unit 180, which enables movement of said cylinder 18 in the x direction, is installed directly below said cylinder 18. The composition and operation of the movable unit 180 are explained later referring to FIG. 3 and FIG. 5.

An electrode unit 190 for fusing the injection needle is installed directly beneath said movable unit 180. The composition and operation of the movable unit 190 are explained later referring to FIG. 3 and FIG. 4.

An exhaust unit 31 for collecting and discharging air in said electrode unit 190 after it has passed through the deodorizing unit 30, is installed on the rear face of the injection needle safety disposal apparatus 100.

A battery 1 which supplies power for fusing the injection needle is installed on the rear face of the injection needle safety disposal apparatus 100.

Figure 3:
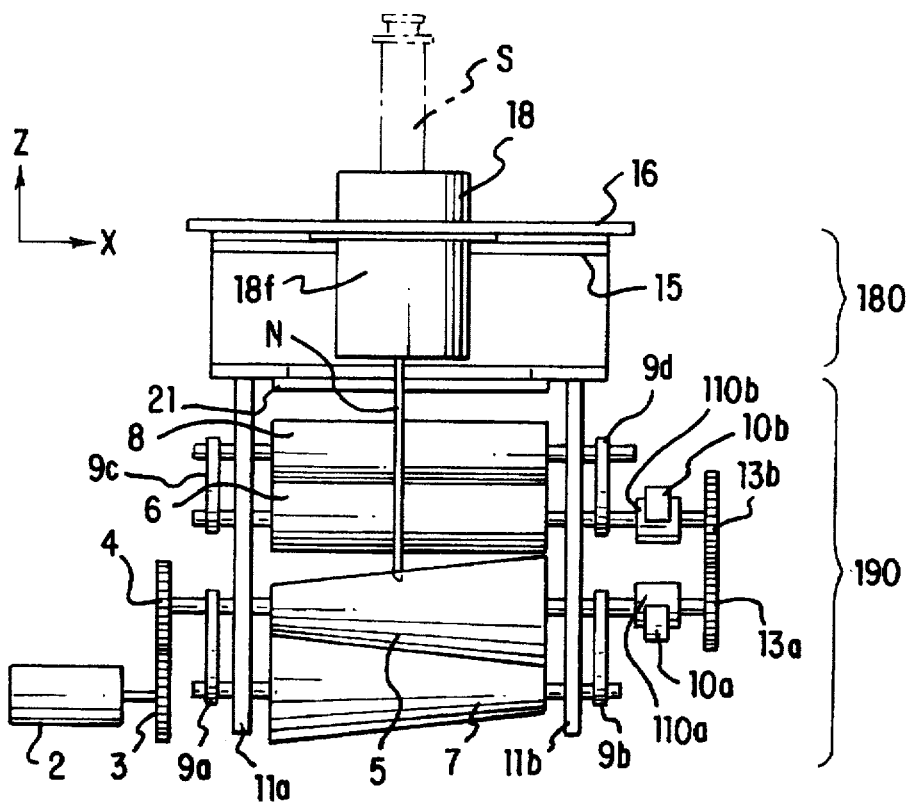
FIG. 3 is an explanatory drawing of the movable unit and the electrode unit.

FIG. 3 is an explanatory drawing of the movable unit 180 and the electrode unit 190.

A guide plate 15 in the movable unit 180 supports only the protruding part in the y direction of flange 18f, which protrudes from the cylinder 18. This arrangement enables the flange 18f to slide on the guide plate 15 in the x direction so that cylinder 18 can move in the x direction.

A spark arresting film 21 is affixed on the base of the movable unit 180.

First roller-type electrode 5 and second roller type electrode 6 are provided in the electrode unit 190. The first roller-type electrode 5 has a tapered shape so that its diameter varies along the direction of the axis of rotation. The second roller-type electrode has a constant diameter throughout the direction of the axis of rotation. On the other hand, the axis of rotation of the first roller-type electrode 5 and the axis of rotation of the second roller type electrode 5 are parallel to each other. Therefore, the gap between the surface of the first roller-type electrode 5 and the second roller-type electrode 6 becomes smaller going toward the right along the direction of the axis of rotation. If said cylinder 18 is positioned to match the scale of said panel 16, the narrow space between the surfaces of roller-type electrodes 5 and 6 can be used for thin injection needles; the wide space between the surface of roller-type electrodes 5 and 6 can be used for thick injection needles.

Materials with small electrical resistance, such as brass or phosphor bronze are recommended as the material for central shafts of said roller-type electrodes 5 and 6. For circumferential surfaces (the parts of the electrode surface that touch the injection needle N) of said roller-type electrodes 5 and 6, materials with small electrical resistance, high melting point, good thermal conductivity are recommended, such as titanium, tungsten, or alloys of materials (for instance, brass or phosphor bronze) containing tungsten and copper or silver. To manufacture the roller-type electrodes 5 and 6, the circumferential surface may be wrapped around the central shaft, or it may be manufactured as a pipe form and press fit onto the central shaft is inserted.

The central shafts of said roller-type electrodes 5 and 6 are provided with slip rings 110a and 110b. The slip rings 110a and 110b are in contact with brushes 10a and 10b to which power is supplied from the battery 1. That is, power from the battery 1 is supplied to the roller-type electrodes 5 and 6 through brushes 10a and 10b, and slip rings 110a and 110b. If the inner surfaces of slip rings 110a and 110b and the surfaces of shafts of the roller-type electrodes 5 and 6 are designed to slide, then both surfaces should preferably be hard-chrome-plated to reductive friction.

The first roller-type electrode 5 is driven and rotated by a DC motor 2 through gears 3 and 4. The second roller-type electrode 6 is driven and rotated by a DC motor 2 through gears 3 and 4, said first roller-type electrode 5 and gears 13a and 13b.

A scraper 7 is provided near the first roller-type electrode 5 for scraping off material deposited on the first roller-type electrode 5. The first roller-type electrode 5 and the scraper 7 are connected by circular belts 9a and 9b, and they rotate in opposite directions with respect to each other. This arrangement enables fused material to be scraped off efficiently.

Also, a scraper 8 is provided near the second roller-type electrode 6 for scraping off material deposited on the second roller-type electrode 6. The second roller-type electrode 6 and the scraper 8 are connected by circular belts 9c and 9d, and they rotate in opposite directions with respect to each other. This arrangement enables fused material to be scraped off efficiently.

The roller-type electrodes 5 and 6, and the scrapers 7 and 8 are supported by support plates 11a and 11b. Use of heat resistant plastics (for instance, thermoplastic polyester based composite sheet) is recommended for said support plates 11a and 11b because heat is transferred from the roller-type electrodes 5 and 6.

The support plates 11a and 11b are fitted such that they can be removed from the movable unit 180. If the support plates 11a and 11b are removed from the movable unit 180, the roller-type electrodes 5 and 6, and scrapers 7 and 8 can be removed; therefore, maintenance work such as cleaning or replacement of these items is improved.

The injection needle N of the syringe S inserted in the cylinder 18 passes through the cylinder 18. The tip of the injection needle N touches the first roller-type electrode 5. The part of the injection needle N slightly away from the tip and toward the root touches the second roller-type electrode 6. The part of the injection needle N that touches the roller-type electrodes 5 and 6 generates Joule heat because of the flow of a large electric current, fuses and falls off; the metal scrap is received and collected in the tray 40. At this stage, in order to position the cylinder 18 to match the scale of the panel 16, if the diameter of the injection needle N is small, the gap between the parts in contact with roller-type electrodes 5 and 6 decreases; if the diameter of the injection needle is large, the gap between the parts in contact with roller-type electrode 5 and 6 increases The resistance value of the part of the injection needle N in contact with the roller-type electrodes 5 and 6 is small if the injection needle N is thick rather than thin when the diameter is considered; however, this value becomes large if said gap is large rather than small when the gap is considered. Therefore, the resistance value does not change appreciably even if the diameter of the injection needle N changes, and the electric current does not flow excessively or poorly, irrespective of the diameter of the injection needle, enabling stable disposal of the injection needle.

Figure 4:
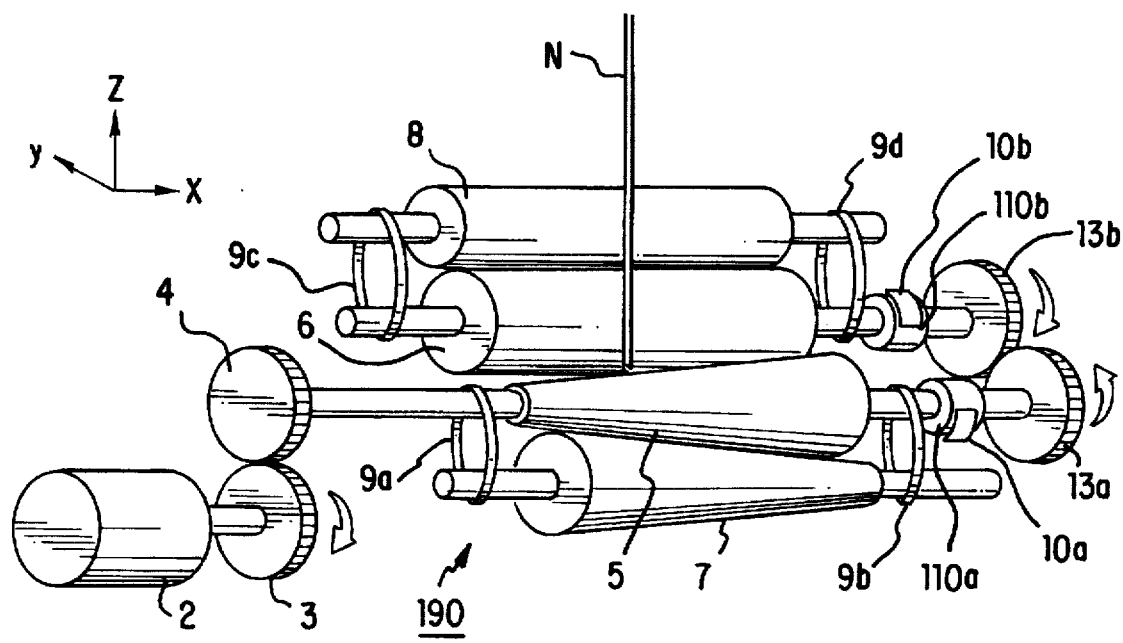
FIG. 4 is a perspective view of the major parts of the electrode unit.

FIG. 4 is a perspective view of the major parts of the electrode unit 190.

The direction of rotation of roller-type electrodes 5 and 6 is such that the injection needle N is pulled in. The direction of rotation is shown by arrows in the figure.

Figure 5:
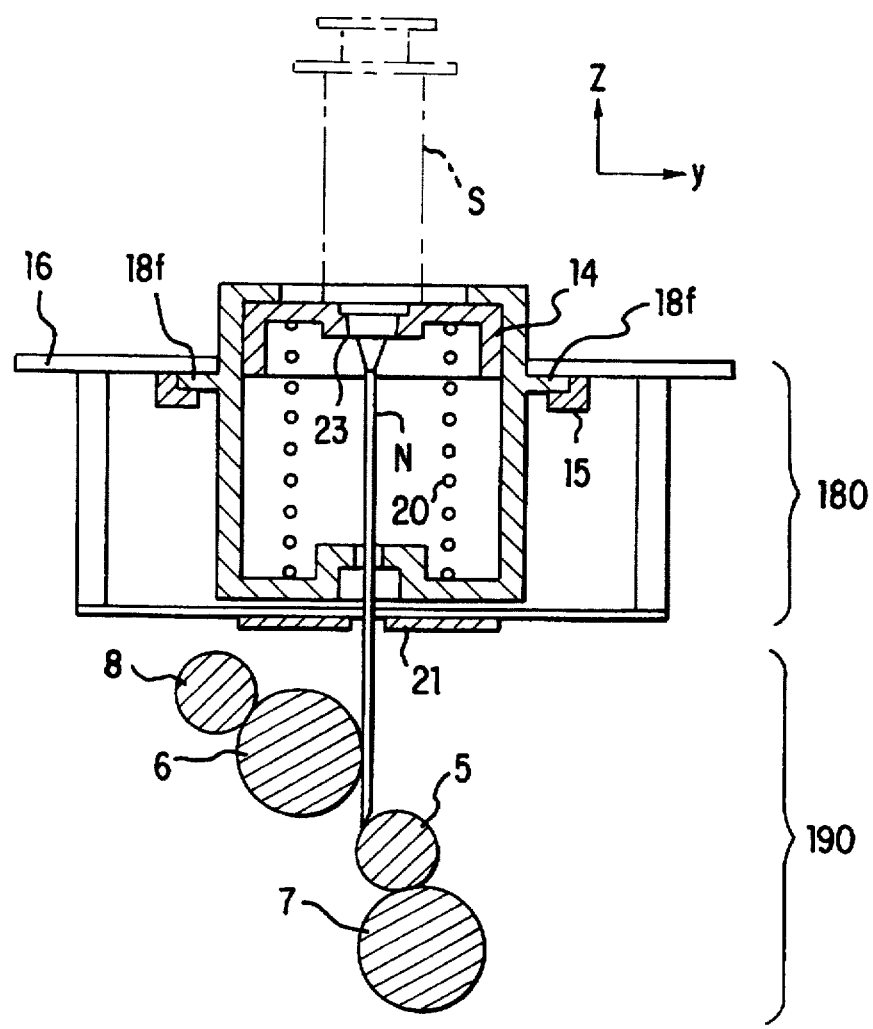
FIG. 5 is a cross-section view showing the internal construction of the cylinder.

FIG. 5 is a cross-section view showing the internal construction of said cylinder 18.

A cover 14 provided inside the cylinder 18 and capable of motion in the vertical direction, is supported by a spring 20. An injection needle insertion hole 23 is drilled in the cover 14. Consequently, when the injection needle N of the syringe S is inserted in the injection needle insertion hole 23, the base of the syringe S adheres closely to the cover 14. When the injection needle N touches the roller-type electrodes 5 and 6, sparks are generated but since these sparks cannot leak out of the injection needle safety disposal apparatus 100, safety is improved.

During the disposal of the injection needle N, the operator pushes in the syringe S while resisting the elastic forces of the spring 20, with the base of the syringe S adhering closely to the cover 14. Thereupon, the tip of the injection needle N touches the second roller-type electrode 6 at the start, then touches the first roller-type electrode 5. Consequently, electric current flows and the tip of the injection needle N is fused. The operator pushes in the syringe S further. Almost the complete injection needle except for a very small part becomes fused and gets converted to metal scrap. The base of the injection needle N fuses and seals off the space, preventing leakage of residue in the syringe S.

Since the roller-type electrodes 5 and 6 are rotating during this process, the parts in contact with the injection needle N change all the time. Moreover, the scrapers 7 and 8 scrape off fused material as soon as it is formed. Therefore, deposition of part of the injection needle N is prevented, degradation of the performance of roller-type electrodes 5 and 6 is prevented, and the life of the electrode is prolonged.

If the roller-type electrodes 5 and 6 are rotated such that the injection needle N is pulled in, it becomes easy to push in the syringe S with a small force. If the injection needle N is stuck between the roller-type electrodes 5 and 6 because of a drop in the voltage of the battery 1, the direction of rotation of the electrodes can be reversed by means of the reverse rotation switch 25, and the injection needle N can be pulled out.

Figure 6:
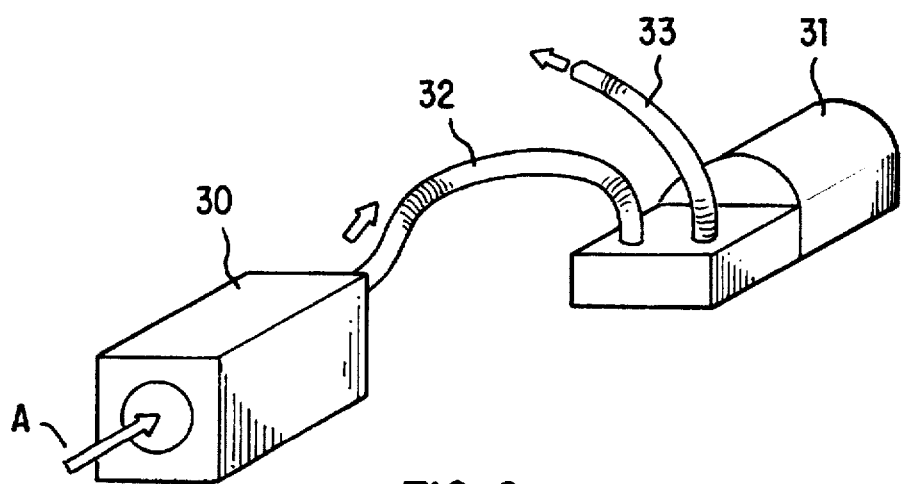
FIG. 6 is an explanatory drawing of the deodorizing unit and the exhaust unit.

FIG. 6 is an explanatory drawing showing the deodorizing unit 30 and the exhaust unit 31.

The deodorizing unit 30 contains deodorizing agents such as activated charcoal, open cellular urethane sheet containing activated charcoal, fibrous activated charcoal, or nonwoven fabric either independently or as a combination of these substances. The deodorizing unit 30 can be removed easily from the injection needle safety disposal apparatus 100 (refer to FIG. 1 and FIG. 2), therefore, the deodorizing agent can be replaced easily.

The exhaust unit 31 sucks air A in the electrode unit 190 through the deodorizing unit 30 and an air intake pipe 32, and discharges it outside the injection needle safety disposal apparatus 100 through an exhaust pipe 33. A positive-displacement type blower or compressor is recommended for use as the exhaust unit 31 rather than a turbo type blower or compressor. This is because the former is compact and is capable of high compression (for instance, obtaining a static pressure equal to or greater than 100 mmH$_2$O) easily, therefore, without sacrifice of the compactness of the injection needle safety disposal apparatus 100, foul odors in the apparatus and gases generated during the fusion of the injection needle can be satisfactorily absorbed and deodorized using deodorizing agents.

By deodorizing and discharging the air and gases generated when the injection fluid or blood residue in the injection needle N is burnt, the spread of foul odors can be prevented.

Figure 7:
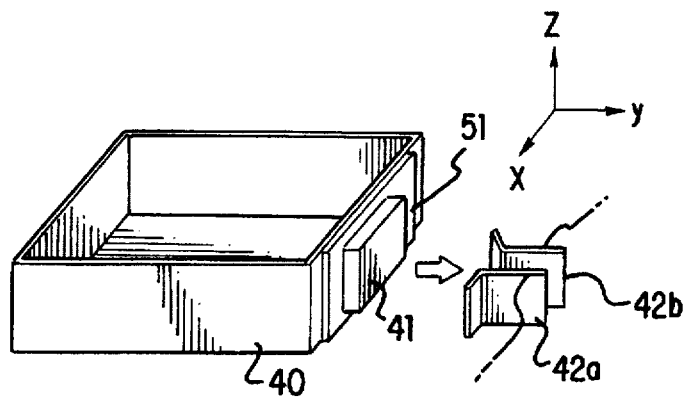
FIG. 7 is an explanatory drawing of the safety switch.

FIG. 7 is an explanatory drawing of the rear face of the tray 40.

An insulated plate 51 is affixed to the rear face of the tray 40. A conductive contact block 41 is fitted to the insulated plate 51.

Meanwhile, a pair of contact plates 42a and 42b are provided inside the injection needle safety disposal apparatus 100. When the tray 40 is fully inserted, the contact block 41 connects the contact plates 42a and 42b making them conductive. The function of a safety switch is realized by using this mechanism (described later). Instead of said mechanism, a limit switch (available in the market) that becomes OFF when the tray 40 is pulled out, can also be used to realize the function of a safety switch.

Figure 8:
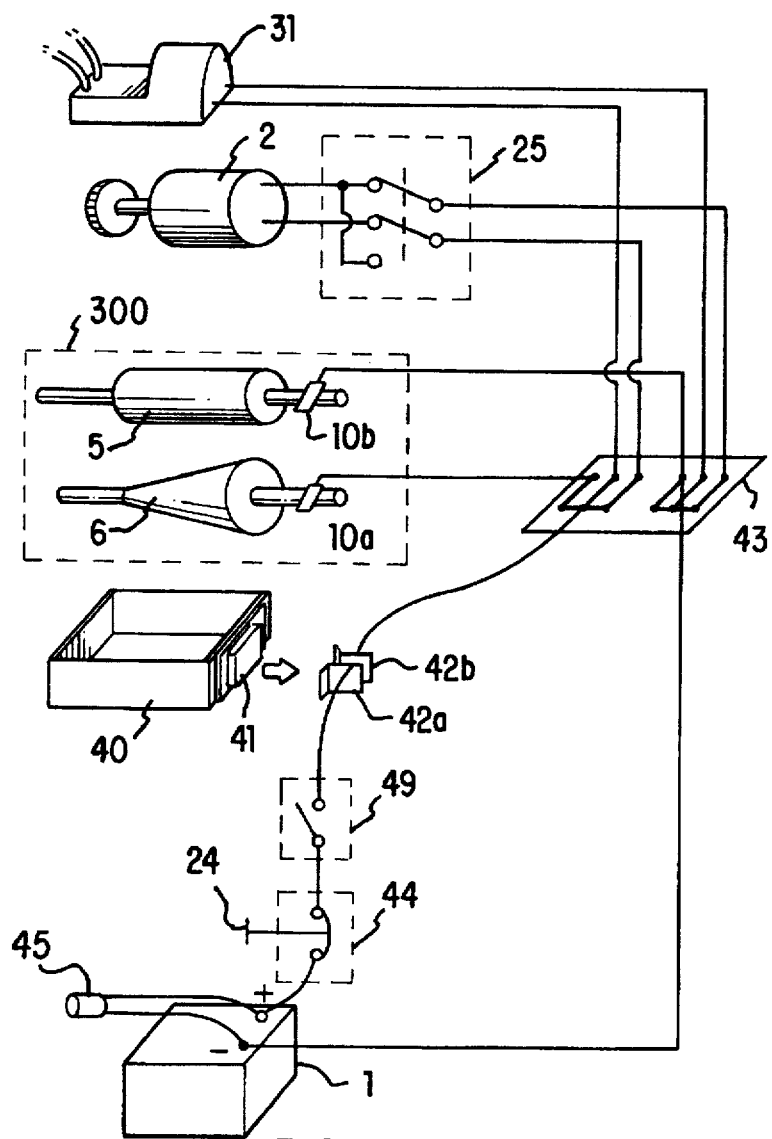
FIG. 8 is a wiring diagram of the injection needle safety disposal apparatus of FIG. 1.

FIG. 8 is the wiring diagram of the injection needle safety disposal apparatus 100.

The battery 1 is connected to a terminal block 43 through a circuit protector 44, a main switch 49 (this is a switch interlocked with the position of the cylinder 18), and contact plates 42a and 42b.

The terminal block 43 is connected to brushes 10a and 10b. The terminal block 43 is also connected to DC motor 2 through the reverse rotation switch 25. The terminal block 43 is also connected to the exhaust unit 31.

Second Embodiment

Figure 9:
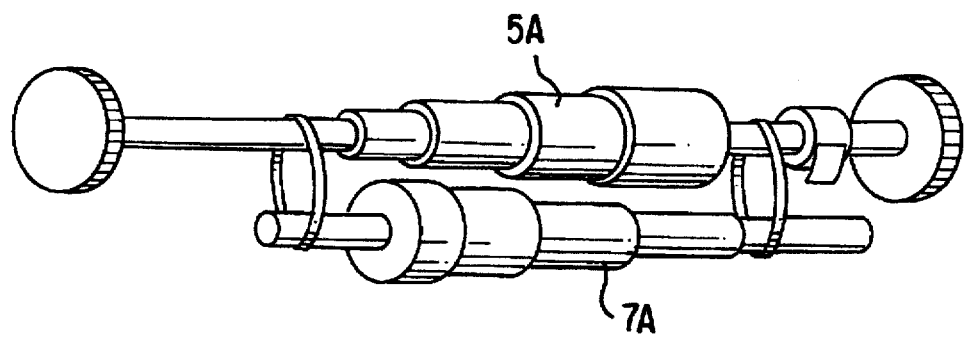
FIG. 9 is a perspective view of the roller-type electrode of the second embodiment of the present invention.

Instead of the tapered shape roller-type electrode 5 and scraper 7 (refer to FIG. 4), a roller-type electrode 5A and a scraper 7A each of which is provided with steps as shown in FIG. 9 may also be used.

This embodiment has the advantage of increasing the range in the x direction for disposing needles of various thicknesses (23G, 21G, 18G, 16G, etc.).

Third Embodiment

Figure 10:
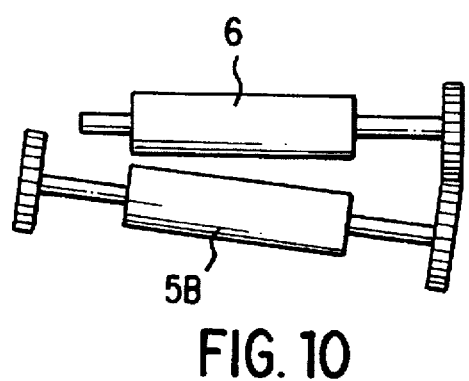
FIG. 10 is an explanatory drawing of the arrangement of roller-type electrodes of the third embodiment of the present invention.

A first roller-type electrode 5B of cylindrical shape with constant diameter and inclined with respect to the roller-type electrode 6 may also be used, as shown in FIG. 10.

This embodiment has the advantage of eliminating the need to use the roller-type electrode 5 with a taper, which is difficult to manufacture.

Fourth Embodiment

Figure 11:
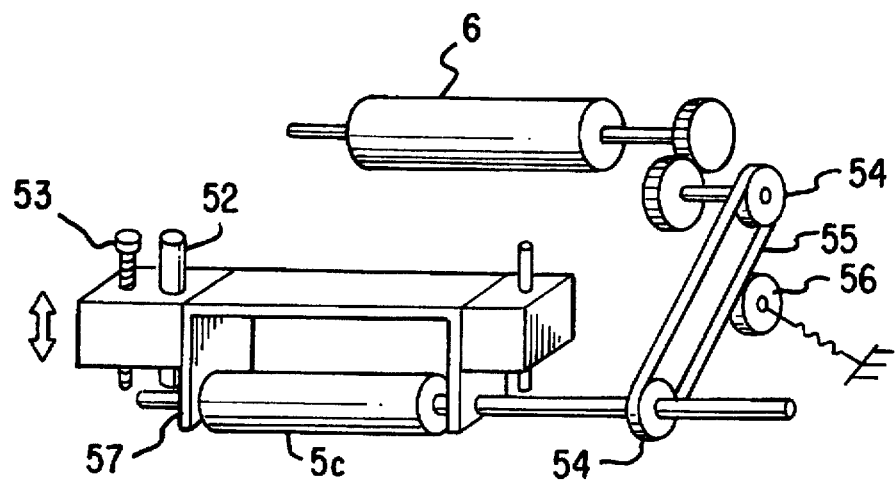
FIG. 11 is a perspective view showing the construction of roller-type electrodes of the fourth embodiment of the present invention.

As shown in FIG. 11, an arrangement wherein, a first roller-type electrode 5C of cylindrical shape with constant diameter is supported by a support fitting 57 capable of motion along a guide shaft 52 by means of a gap adjustment screw 53, enabling the gap between the first roller-type electrode 5C and the second roller-type electrode 6 to be adjusted, may also be provided. Rotation can be transferred to the second roller-type electrode 6 through pulleys (or sprockets) 54, a timing belt (or chain) 55, and an idler roller 56.

This embodiment has the advantage that the operator can easily set a gap that is optimum for the thickness of the injection needle.

Fifth Embodiment

Figure 12:
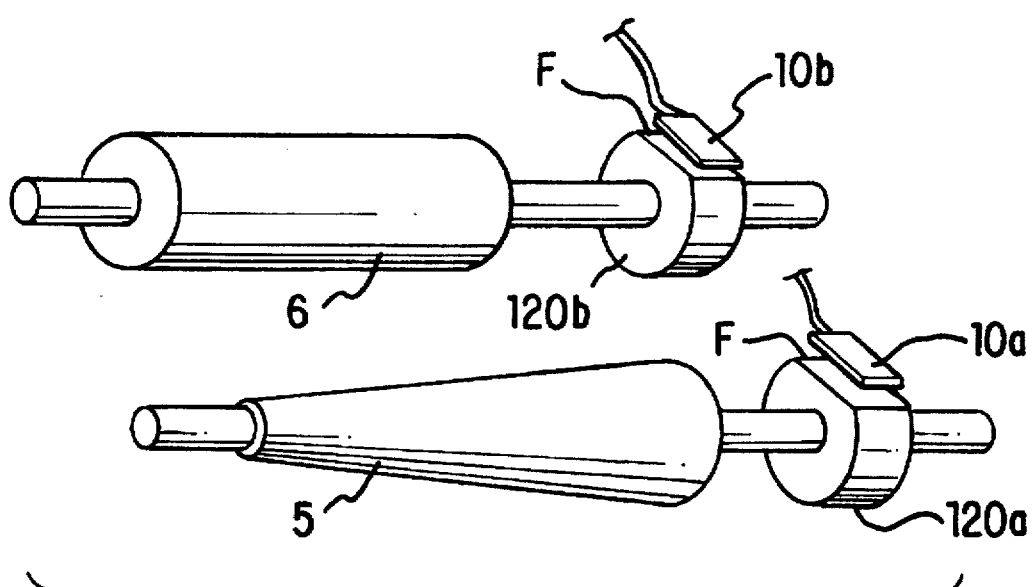
FIG. 12 is an explanatory drawing of the slip ring of the fifth embodiment of the present invention.

Cam-shaped slip rings 120a and 120b provided with notched parts F, as shown in FIG. 12 may also be used.

At the notched parts F, the brushes 10a and 10b and the slip rings 120a and 120b break contact (or the contact pressure becomes small resulting in an increase in contact resistance), therefore an intermittent pulse electric current (or a periodically small electric current) can be made to flow to the injection needle. Since the power consumption reduces, the life of the battery 1 can be prolonged by this arrangement. Moreover, since a small electric current is used, damage to the roller-type electrode 5 and 6 can also be reduced.

Sixth Embodiment

Figure 13A:
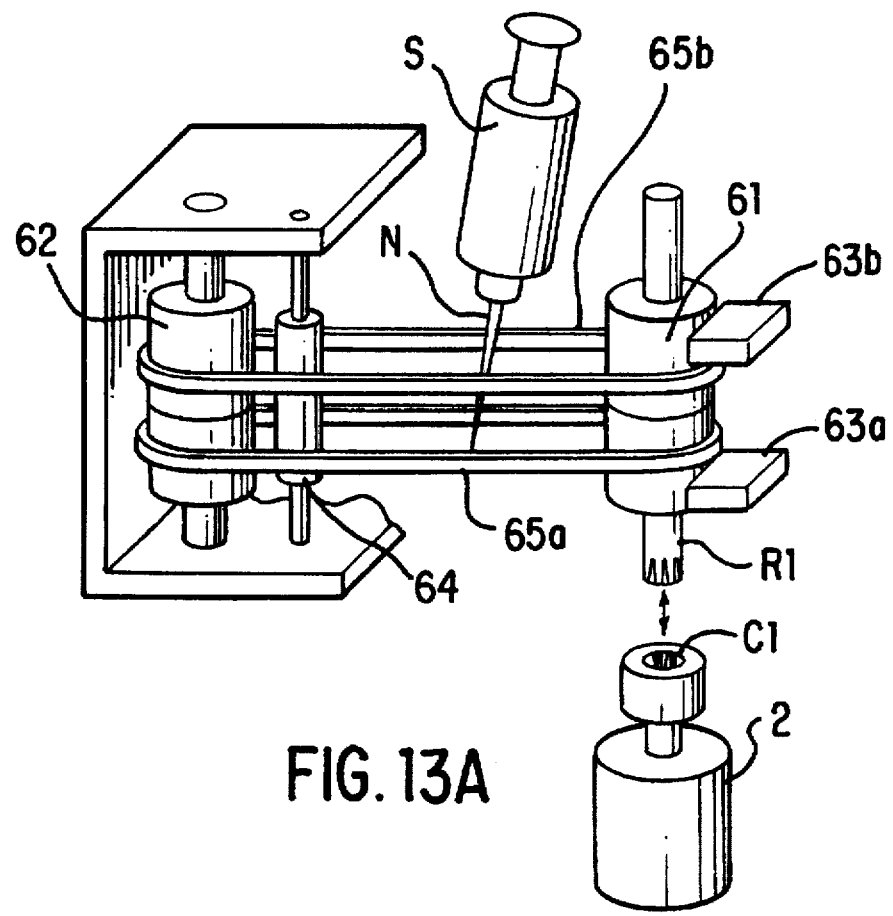
FIG. 13A and FIG. 13B are explanatory drawings of the electrode unit of the sixth embodiment of the present invention.
Figure 13B:
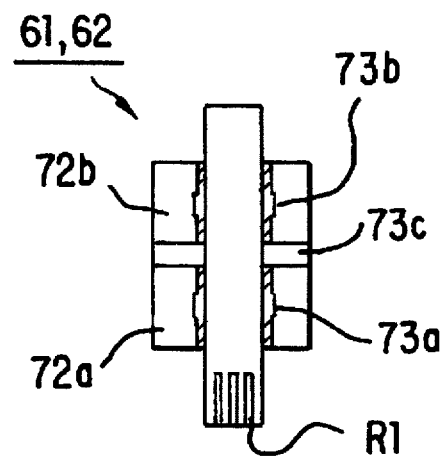
Figure 14:
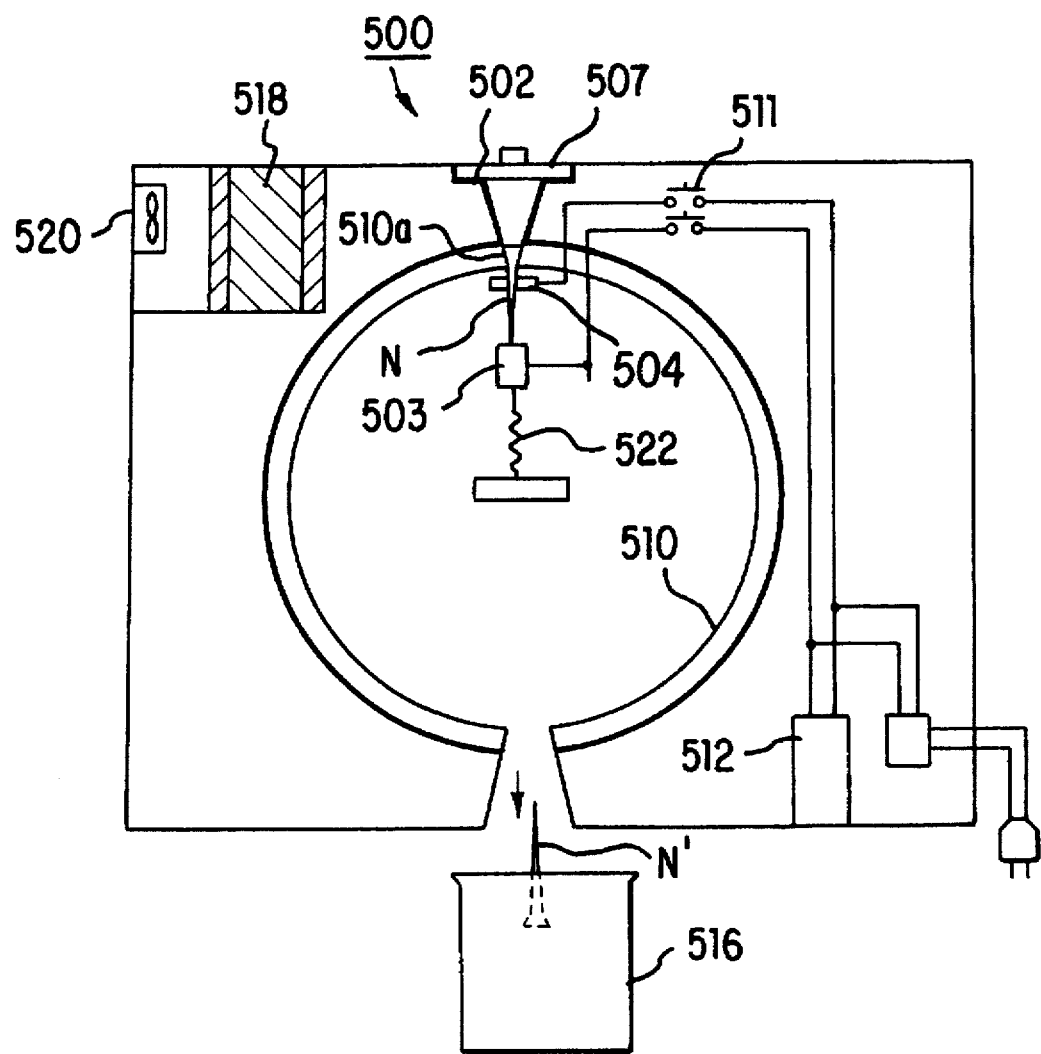
FIG. 14 is an explanatory drawing showing an example of the injection needle safety disposal apparatus of prior art.

As shown in FIG. 13A, metal wires (or metal belts) 65a and 65b are stretched between a pair of rollers 61 and 62. Rollers 61 and 62, as shown a cross-section view in FIG. 13B, and contact parts 72a and 72b of metal wires 65a and 65b, are made of a conducting metal. Also, said contact parts 72a and 72b are insulated by means of insulated sleeves 73a and 73b, and insulated disc 73. Contacts 63a and 63b are brought in close contact with the contact parts 72a and 72b and power is supplied.

The injection needle N of the syringe S is inserted between the metal wires 65a and 65b. The tip of the injection needle N is brought into contact with the internal surface of the metal wire 65a at the front.

Power is supplied through the metal wires 65a and 65b, this enables fusing the injection needle N.

The roller 62 is rotated by engagement of serration R1 in the roller 62 with the coupling C1 fitted to DC motor 2. A file 64 scrapes off material deposited on the metal wires 65a and 65b. This enables the life of the metal wires 65a and 65b to be prolonged.

If the diameter of the roller 61 is made different from the diameter of the roller 62, the gap between the internal surface of the metal wire 65a at the front side and the internal surface of the metal wire 65b at the far side will vary depending on the position, therefore various thicknesses of injection needle N can be used.

Seventh Embodiment

A torque limiter may be fitted on the rotating shaft of gear 3 of DC motor 2, and the DC motor made to rotate only in one direction without providing the reverse rotation switch 25. According to this embodiment, when the injection needle is at the point of being engaged between roller-type electrodes 5 and 6, since the DC motor 2 is running idle, the injection needle is no longer engaged with a strong force. Moreover, the injection needle can be pulled out easily.

In this way, according to the present invention of the injection needle safety disposal apparatus, by moving the electrodes, the parts of electrodes in contact with the injection needle can be varied all the time so that deposition of the fused part of the injection needle on the electrode becomes difficult, degradation in performance of electrode is prevented, the life of the electrode is prolonged and maintenance work becomes easy.

What is claimed is:

1. An injection needle safety disposal apparatus comprising a first roller electrode with a contact part that touches the tip of the injection needle, a second roller electrode with a contact part that touches a part on said injection needle located away from the tip and toward the root of the needle, an electrode moving means for rotating said first roller electrode and said second roller electrode to change the contact part of said first roller electrode and said second roller electrode, and a power supply means for supplying power to said first roller electrode and said second roller electrode to provide for fusing a part of said injection needle when it touches the contact part of said rotating first roller electrode and the contact part of said rotating second roller electrode.

2. An injection needle safety disposal apparatus according to claim 1 further comprising scraping means for scraping off material deposited on at least one of the first and second roller electrodes provided juxtaposed to at least one of said first and second roller electrodes.

3. An injection needle safety disposal apparatus according to claim 2 wherein said scraping means has a frustro-conical configuration.

4. An injection needle safety disposal apparatus according to claim 2 wherein said scraping means is a rotatable roller.

5. An injection needle safety disposal apparatus according to claim 4 further comprising means enabling insertion of a needle in the injection needle safety disposal apparatus in an insertion direction, and means for changing a width of a gap between said first roller electrode and said second roller electrode in a direction insersecting said insertion direction.

6. An injection needle safety disposal apparatus according to claim 4 wherein a width of a gap between said first roller electrode and said second roller electrode varies along the axes of the first and second roller electrodes.

7. An injection needle safety disposal apparatus according to claim 1 further comprising means enabling insertion of a needle in the injection needle safety disposed apparatus in an insertion direction, and means for changing a width of a gap between said first roller electrode and said second roller electrode in a direction intersecting said insertion direction.

8. An injection needle safety disposal apparatus according to claim 7 further comprising covering means having an injection needle insertion hole such that when an injection needle is inserted in said injection needle insertion hole, the base of a syringe provided with the injection needle closely adheres to a portion of the covering means surrounding said injection needle insertion hole to thereby isolate the inside of the injection needle safety disposal apparatus from the ambient, said cover means moving up or down following the motion of the syringe when said syringe is pushed in or pulled our of the injection needle safety disposal apparatus.

9. An injection needle safety disposal apparatus according to claim 7 further comprising tray means which receives and collects fused and hardened materials that drop after they are generated when a part of the injection needle fuses, said tray means being removable from the injection needle safety disposal apparatus, and safety switch means for disabling said power supply means when the tray means has been removed from the injection needle safety disposal apparatus.

10. An injection needle safety disposal apparatus according to claim 7 further comprising deodorizing means and exhaust means for discharging the air in the vicinity of said electrodes after said air has been led to said deodorizing means and deodorized, said exhaust means being a positive-displacement pump.

11. An injection needle safety disposal apparatus according to claim 1 wherein a width of a gap between said first roller electrode and said second roller electrode varies along the axes of the first and second roller electrodes.

12. An injection needle safety disposal apparatus according to claim 11, further comprising means enabling insertion of a needle in the injection needle safety disposal apparatus in an insertion direction, means for changing a width of a gap between said first roller electrode and said second roller electrode in a direction intersecting the direction of insertion of the injection needle, said means enabling insertion of a needle in the injection needle safety apparatus in said insertion direction comprising covering means having an injection needle insertion hole such that when an injection needle is inserted in said injection needle insertion hole, the base of a syringe provided with an injection needle closely adheres to a portion of the covering means surrounding the injection needle insertion hole to thereby isolate the inside of the injection needle safety disposal apparatus from the ambient, said covering means moving up or down following the motion of the syringe when said syringe is pushed in or pulled our of the injection needle safety disposal apparatus.

13. An injection needle safety disposal apparatus according to claim 11 further comprising tray means which receives and collects fused and hardened materials that drop after the fused and hardened materials are generated when a part of the injection needle fuses, said tray means being removable from the injection needle safety disposal apparatus, and safety switch means for disabling said power supply means when the tray means has been removed from the injection needle safety disposal apparatus.

14. An injection needle safety disposal apparatus according to claim 11 further comprising deodorizing means and exhaust means for discharging the air in the vicinity of said electrodes after said air has been led to said deodorizing means and deodorized, said exhaust means being a positive-displacement pump.

15. An injection needle safety disposal apparatus according to claim 1 wherein said first roller electrode has a uninterrupted outer circular surface which defines said contact part which touches the tip of the injection needle.

16. An injection needle safety disposal apparatus according to claim 1 wherein said second roller electrode has a uninterrupted outer circular surface which defines said contact part which touches the tip of the injection needle.

17. An injection needle safety disposal apparatus according to claim 16 wherein the second roller electrode touches the injection needle with a tangential relationship.

18. An injection needle safety disposal apparatus according to claim 1 wherein said first roller electrode is disposed to substantially tangentially touch said injection needle.

19. An injection needle safety disposal apparatus according to claim 1 wherein said needle has a longitudinal needle axis, said needle when in said safety disposal apparatus having its axis disposed in a first direction, said needle axis defining an imaginary plane which contains said needle axis and which is substantially perpendicular to the axis of at least one of said first and second roller electrodes, said first and second roller electrodes being disposed on opposite sides of said imaginary plane, said first and second roller electrodes being longitudinally spaced from one another along said longitudinal needle axis.

20. An injection needle safety disposal apparatus according to claim 1 wherein at least one of said first and second roller electrodes has a frustro-conical configuration.

21. An injection needle safety disposal apparatus according to claim 1 wherein said first roller electrode has an axis of rotation disposed at an acute angle relative to the axis of rotation of said second roller electrode.

22. An injection needle safety disposal apparatus according to claim 1 wherein said first and second roller electrodes each have a plurality of cylindrical portions with the diameters of the cylindrical portions of said first roller electrode being different from one another and the diameters of the cylindrical portions of the second roller electrode being different from one another.

23. An injection needle safety disposal apparatus comprising a first electrode with a contact part that touches the tip of the injection needle, a second electrode with a contact part that touches a part of said injection needle located away from the tip and toward the root of the needle, a pair of spaced rollers, said first and second electrodes comprising first and second endless electrode members disposed about and driven by said rollers, and power supply means for supplying power to said first endless electrode member and to said second endless electrode member to thereby provide for fusing a part of said injection needle when said injection needle touches the contact part of said first endless electrode member and said contact part of said second endless electrode member.

24. An injection needle safety disposal apparatus according to claim 23 wherein each of said spaced pair of rollers have different diameters.

25. An injection needle safety disposal apparatus comprising a first electrode with a contact part that touches the tip of the injection needle, a second electrode with a contact part that touches a part on said injection needle slightly away from the tip and toward the root of the needle, electrode moving means for moving said first electrode and said second electrode to change the contact part of said first electrode and said second electrode, power supply means for supplying power to said first electrode and said second electrode capable of fusing a part of said injection needle when it touches the contact part of said first electrode and the contact part of said second electrode, at least one electrode from said first electrode and said second electrode is a loop electrode, said electrode moving means is a loop rotating means for rotating said loop electrode.

26. An injection needle safety disposal apparatus according to claim 25 further comprising scraping means for scraping off deposited material from at least one of said first and second roller electrodes, said scraping means being provided near said at least one of said first and second roller electrodes.

27. An injection needle safety disposal apparatus according to claim 26 further comprising means for changing the gap between said first roller electrode and said second roller electrode in a direction intersecting the direction of insertion of the injection needle.

28. An injection needle safety disposal apparatus according to claim 25 further comprising means for changing the gap between said first roller electrode and said second roller electrode in a direction intersecting the direction of insertion of the injection needle.

29. An injection needle safety disposal apparatus comprising a first electrode with a contact part that touches the tip of the injection needle, a second electrode with a contact part touches a part on said injection needle slightly away from the tip and toward the root of the needle, electrode moving means for moving said first electrode and said second electrode to change the contact part of said first electrode and said second electrode, power supply means for supplying power to said first electrode and said second electrode capable of fusing a part of said injection needle when it touches the contact part of said first electrode and the contact part of said second electrode, at least one electrode from said first electrode and said second electrode is a roller electrode, said electrode moving means is a roller rotating means for rotating said roller electrode, at least one electrode from said first electrode and said second electrode is a loop electrode, said electrode moving means is a loop rotating means for rotating said loop electrode.

30. An injection needle safety disposal apparatus according to claim 29 further comprising scraping means for scraping off deposited material from at least one of said first and second roller electrodes, said scraping means being provided near said at least one of said first and second roller electrodes.

31. An injection needle safety disposal apparatus according to claim 30 further comprising means for changing the gap between said first roller electrode and said second roller electrode in a direction intersecting the direction of insertion of the injection needle.

32. An injection needle safety disposal apparatus according to claim 29 further comprising means for changing the gap between said first roller electrode and said second roller electrode in a direction intersecting the direction of insertion of the injection needle.

* * * * *